United States Patent
Feige et al.

(10) Patent No.: US 12,317,913 B2
(45) Date of Patent: *Jun. 3, 2025

(54) DIETARY BUTYRATE

(71) Applicant: SOCIETE DES PRODUITS NESTLE S.A., Vevey (CH)

(72) Inventors: Jerome Feige, Crissier (CH); Elizabeth Forbes-Blom, Epalinges (CH); Joris Michaud, Lausanne (CH); Amaury Patin, Lausanne (CH); Claire Boutry, Villars Burquin (CH); Pascal Stuelsatz, Crissier (CH)

(73) Assignee: Societe des Produits Nestle S.A., Vevey (CH)

( * ) Notice: Subject to any disclaimer, the term of this patent is extended or adjusted under 35 U.S.C. 154(b) by 744 days.

This patent is subject to a terminal disclaimer.

(21) Appl. No.: 17/595,530

(22) PCT Filed: May 20, 2020

(86) PCT No.: PCT/EP2020/064062
§ 371 (c)(1),
(2) Date: Nov. 18, 2021

(87) PCT Pub. No.: WO2020/234345
PCT Pub. Date: Nov. 26, 2020

(65) Prior Publication Data
US 2022/0251470 A1    Aug. 11, 2022

(30) Foreign Application Priority Data
May 21, 2019 (EP) .................................. 19175550

(51) Int. Cl.
| | | |
|---|---|---|
| *A23L 33/115* | (2016.01) | |
| *A23L 29/00* | (2016.01) | |
| *A61K 31/22* | (2006.01) | |
| *A61K 31/231* | (2006.01) | |
| *A61P 21/00* | (2006.01) | |
| *A61P 43/00* | (2006.01) | |
| *C11C 3/00* | (2006.01) | |
| *C11C 3/10* | (2006.01) | |

(52) U.S. Cl.
CPC ............. *A23L 33/115* (2016.08); *A23L 29/00* (2016.08); *A23L 29/04* (2016.08); *A61K 31/22* (2013.01);
(Continued)

(58) Field of Classification Search
CPC ......... C11C 3/10; A61K 31/22; A61K 31/231; A61P 21/00; A61P 43/00; A23L 33/115; A23V 2200/316
See application file for complete search history.

(56) References Cited

U.S. PATENT DOCUMENTS

| | | | | |
|---|---|---|---|---|
| 5,258,197 A | * | 11/1993 | Wheeler ................. | A23G 3/343 426/660 |
| 2008/0248994 A1 | * | 10/2008 | Sartorelli ............... | A61K 31/00 514/557 |
| 2015/0173405 A1 | * | 6/2015 | Van Der Beek ..... | A61K 35/655 426/585 |

FOREIGN PATENT DOCUMENTS

| | | |
|---|---|---|
| JP | 4620740 B2 | 1/2011 |
| WO | 2006085346 | 8/2006 |

OTHER PUBLICATIONS

Lee et al., "High Performance Liquid Chromatographic Separation of Interesterified Palm Oil with Tributyrin", LWT—Food Science and Technology, vol. 41, Issue No. 8, Dec. 31, 2008, pp. 1446-1451.
(Continued)

*Primary Examiner* — Yate' K Cutliff
(74) *Attorney, Agent, or Firm* — K&L Gates LLP (57) ABSTRACT

A compound having the formula (1), (2), (3), or (4), or combinations thereof, for use to maintain or increase muscle function and/or mass in a subject, and/or prevent or reduce muscle wasting in a subject, wherein $R^1$, $R^2$, $R^3$, $R^4$, $R^5$ and $R^6$ are independently, a long chain fatty acid having between 16 and 20 carbons.

(Continued)

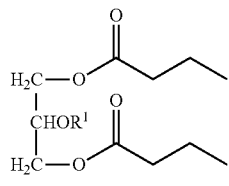

(1)

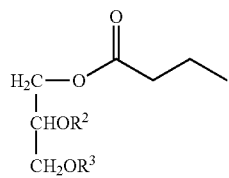

(2)

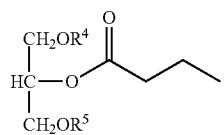

(3)

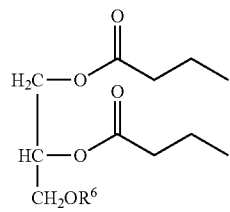

(4)

21 Claims, 3 Drawing Sheets

(52) U.S. Cl.
CPC ............ *A61K 31/231* (2013.01); *A61P 21/00* (2018.01); *A61P 43/00* (2018.01); *C11C 3/003* (2013.01); *C11C 3/10* (2013.01); *A23V 2200/316* (2013.01)

(56) References Cited

OTHER PUBLICATIONS

Chinese Office Action for Appl No. 202080036927.4 dated Jul. 20, 2023.
Hayes et al. "Review of Triacylglycerol Digestion, Absorption, and Metabolism with Respect to SALATRIM Triacylglycerols" Journal of Agricultural and Food Chemistry, 1994, vol. 42, No. 2, pp. 474-483.
Sampugna et al. "Digestion of Butyrate Glycerides by Pancreatic Lipase" Lipids, 1967, vol. 2, No. 5, pp. 397-402.
Jensen et al. "Symposium: Milk Fat-Composition, Function, and Potential for Change—The Composition of Milk Fat" J Dairy Sci, 1991, vol. 74, pp. 3328-3243.
Japanese Office Action for Appl No. 2021-563171 dated Jun. 25, 2024, 4 pages.

* cited by examiner

DIETARY BUTYRATE

CROSS REFERENCE TO RELATED APPLICATIONS

The present application is a National Stage of International Application No. PCT/EP2020/064062, filed on May 20, 2020, which claims priority to European Patent Application No. 19175550.3, filed on May 21, 2019, the entire contents of which are being incorporated herein by reference.

FIELD OF THE INVENTION

The present invention relates to a dietary source of butyrate having improved organoleptic properties for use in increasing muscle function and/or muscle mass. For example, the present invention is useful for subjects to promote muscle repair and/or subjects suffering from pre-cachexia, cachexia, sarcopenia, myopathy, dystrophy and/or recovery after muscle injury or surgery.

BACKGROUND TO THE INVENTION

Skeletal muscle regeneration is a crucial mechanism to repair and maintain muscle mass and function throughout life. Skeletal muscle regeneration primarily requires the participation of myogenic progenitors, known as muscle stem cells or satellite cells.

Non-proliferative, quiescent satellite cells, which adjoin resting skeletal muscles, can be identified by their distinct location between sarcolemma and basal lamina, a high nuclear-to-cytoplasmic volume ratio, few organelles (e.g. ribosomes, endoplasmic reticulum, mitochondria, golgi complexes), small nuclear size, and a large quantity of nuclear heterochromatin relative to myonuclei. On the other hand, activated satellite cells have an increased number of caveolae, cytoplasmic organelles, and decreased levels of heterochromatin.

These muscle satellite cells are part of the adult stem cell niche and they are involved in the normal growth of muscle, as well as regeneration following injury or disease. Hence, they are a potential target to enhance muscle regeneration in both healthy and diseased conditions. Skeletal muscle regeneration follows a series of steps that recapitulates the phases of development. Muscle progenitor cells must exit the state of quiescence and become active, proliferate and commit to myogenic differentiation.

These different steps can be monitored following the expression of specific transcription factors. Satellite cells express genetic markers at different stages of myogenesis and proliferation. The myogenic regulatory factors Pax7 and MyoD are the major hallmarks of muscle stem cell stemness and commitment and can be used to monitor muscle stem cell progeny. In particular, Pax7 marks early amplification while MyoD is a later marker for myogenic commitment, and combinations of these markers define the different states of proliferation, differentiation and self-renewal. For example, activated satellite cells expressing low levels of Pax7 are more committed to differentiation, whereas high levels of Pax7 are related to cells less prone to differentiate and have more undifferentiated stemness characteristics. Activation and the induction of myogenesis is typically regulated by myogenic regulatory factors such as MyoD, Myf5, myogenin and MRF4. Negative regulation by myostatin and TGFb inhibits the differentiation of satellite cells (Almeida et al., Stem Cells Int. (2016), 2016, 1078686).

Enhancing the commitment toward the myogenic differentiation (Pax7−/MyoD+ cells), is particularly relevant in the context of cancer cachexia where a defect in myogenic commitment has been revealed as a potential cause of the muscle wasting (He et al., J Clin Invest. (2013), 123(11), pp 4821-4835).

The current standard of care to counteract muscle wasting is physiotherapy. Experimental therapies which have previously included myoblast transplantation have not been entirely successful due to the reduced regenerative potential of myoblasts which are more committed and differentiated in comparison the muscle stem cells. There are currently no approved drugs to treat muscle-wasting diseases. Nutritional interventions aimed at counteracting muscle wasting largely rely on high protein content in order to boost muscle anabolism, and supplementation with omega 3, vitamin D and anti-oxidants. However, these have shown limited efficacy.

In preclinical studies butyrate has been shown to improve age related muscle decline (Walsh et al., *Ageing Cell* (2015), 14, pp 957-970) and prevent the loss of muscle after neurogenic muscle atrophy (Walsh et al., *Muscle & Nerve* (2015) pp 859-868). In other preclinical studies butyrate has been reported to promote muscle growth in neonatal piglets (Murray et al. *Physiological Reports*, (2018), 6, 10, e13706, pp 1-11).

Common sources of butyrate are butyric acid and tributyrin, a triglyceride made of three ester functional groups with three butyrate moieties and the glycerol backbone. Butyric acid and tributyrin are both food additives that are generally regarded as safe (GRAS) (21CFR582.60 and 21CFR184.1903 respectively), and are natural components of many dairy items. However, butyric acid is associated with negative sensory qualities such as vomit-like, fecal, and cheesy aroma attributes. Tributyrin also has negative sensory qualities, in particular high bitterness. These unpleasant taste and odor attributes can make the oral administration of compositions including these compounds particularly difficult. Butyrate components from dairy cannot be enriched and thus significant volumes of dairy fat would need to be consumed which is not feasible for practical and nutritional reasons, not least as it would lead to large amount of unwanted calorie derived from animal fat.

While butyrate could be beneficial for improving muscle function, today, there is no method to deliver butyrate in a form that has acceptable organoleptic properties.

Accordingly, it would be beneficial to provide a food-grade source of butyrate having improved organoleptic properties as compared to available solutions for use in for maintaining muscle health and improving muscle regeneration.

SUMMARY OF THE INVENTION

The present invention provides compounds that are a source of butyrate having improved organoleptic properties for use in for maintaining muscle health and improving muscle regeneration, in particular in increasing muscle function and/or muscle mass. In particular, the compounds have improved odor and/or taste relative to butyric acid, butyrate salts and/or tributyrin. The compounds may be used as a dietary source of butyric acid. The compounds may be used in, for example, nutritional compositions, dietary supplements, beverages and pet care products.

The compounds and compositions may be used to modulate skeletal muscle function and improve skeletal muscle regeneration in order improve muscle repair after injury or to counteract muscle wasting that occurs in a number of pathological conditions, in particular, cachexia and sarcopenia.

According to a first aspect of the present invention there is provided a compound having the formula or combinations thereof, for use to maintain or increase muscle function and/or mass in a subject, and/or prevent or reduce muscle wasting in a subject, wherein $R^1$, $R^2$, $R^3$, $R^4$, $R^5$ and $R^6$ are independently, a long chain fatty acid having between 16 and 20 carbons.

According to another aspect of the present invention there is provided a composition comprising a compound having the formula (1), (2), (3) or (4) or combinations thereof, for use to maintain or increase muscle function and/or mass in a subject, and/or prevent or reduce muscle wasting in a subject, wherein $R^1$, $R^2$, $R^3$, $R^4$, $R^5$ and $R^6$ are independently, a long chain fatty acid having between 16 and 20 carbons.

In one embodiment, the composition comprises the compound having formula (1), the compound having formula (2), the compound having formula (3) and the compound having formula (4).

The composition may comprise the compound having formula (1) and the compound having formula (2).

The composition may comprise the compound having formula (1) and the compound having formula (3).

The composition may comprise the compound having formula (1) and the compound having formula (4).

The composition may comprise the compound having formula (2) and the compound having formula (3).

The composition may comprise the compound having formula (2) and the compound having formula (4).

The composition may comprise the compound having formula (3) and the compound having formula (4).

The composition may comprise the compound having formula (1) the compound having formula (2), and the compound having formula (3).

The composition may comprise the compound having formula (1) the compound having formula (2), and the compound having formula (4).

The composition may comprise the compound having formula (1) the compound having formula (3), and the compound having formula (4).

The composition may comprise the compound having formula (2) the compound having formula (3), and the compound having formula (4).

The composition may comprise the compound having formula (1), the compound having formula (2), the compound having formula (3) and the compound having formula (4).

In one embodiment the compounds having formula (1), (2), (3) and (4), comprise at least 50%, 60%, 70%, 80%, 90%, 95% or 99% by weight of the total triglycerides of the composition.

In one embodiment the compounds having formula (1), (2), (3) and (4), comprise at least 50%, 60%, 70%, 80%, 90%, 95% or 99% by weight of the total butyrate moiety containing triglycerides in the composition.

In one embodiment tributyrin comprises less than 10% by weight of the total triglycerides in the composition, preferably less than 8% by weight, more preferably less than 5% by weight of the total triglycerides in the composition.

In one embodiment the composition further comprises vitamin A and/or dietary fiber and/or probiotic.

The composition of the invention may be in the form of a nutritional composition, for instance a food, a beverage, a pet care product.

The composition of the invention may be in the form of a dietary supplement.

In one embodiment $R^1$, $R^2$, $R^3$, $R^4$, $R^5$ and/or $R^6$ is an unsaturated fatty acid, preferably monounsaturated.

In one embodiment $R^1$, $R^2$, $R^3$, $R^4$, $R^5$ and/or $R^6$ is selected from the group consisting of oleic acid, palmitic acid, or linoleic acid, preferably each of $R^1$, $R^2$, $R^3$, $R^4$, $R^5$ and $R^6$ is oleic acid.

The compounds and compositions of the present invention, may be useful for modulating muscle stem cell function to maintain or increase skeletal muscle function and/or mass in a subject, and/or substantially prevent or reduce muscle wasting in a subject. In particular, to enhance: the number of muscle stem cells, the function of muscle stem cells, myogenesis and muscle growth.

The compounds and compositions of the present invention, may be useful to promote muscle regeneration, recovery from muscle wasting or muscle injury, and/or to prevent or treat sarcopenia or cachexia; or precachexia. In particular, wherein sarcopenia is loss of muscle mass and/or strength linked to aging and cachexia is associated with a disease, for example, when associated with cancer, chronic heart failure, renal failure, chronic obstructive pulmonary disease, AIDS, autoimmune disorders, chronic inflammatory disorders, cirrhosis of the liver, anorexia, chronic pancreatitis, metabolic acidosis and/or neurodegenerative disease (Von Haehling et al., J Cachexia Sarcopenia Muscle (2014), 5(4), pp 261-263).

In one embodiment the compounds or combinations thereof have improved organoleptic properties relative to butyric acid, tributyrin and/or butyrate salts.

In one embodiment the compounds is provided to a mammal, preferably, a human, a pet or a farm animal.

BRIEF DESCRIPTION OF THE DRAWINGS

FIG. 3 shows the myogenic commitment of muscle stem cells treated with sodium butyrate.

DETAILED DESCRIPTION OF THE INVENTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

Triglycerides

A triglyceride (also known as a triacylglycerol) is a triester that is derived from glycerol and three fatty acids. Under hydrolysis conditions such as those during digestion, triglycerides may be a source of fatty acids. For instance, tributyrin is potentially a source of three moles of butyric acid per mole of tributyrin.

Fatty acids are carboxylic acids with a long tail (chain). Fatty acids may be either unsaturated or saturated. Fatty acids which are not attached to other molecules are referred to as free fatty acids (FFA).

The term "fatty acid moiety" refers to the part of the triglyceride that originates from a fatty acid in an esterification reaction with glycerol. The triglycerides used in the present invention comprise at least one butyric acid moiety and at least one long chain fatty acid moiety.

Preferred long chain fatty acids for use in the present invention are fatty acids that have 16 to 20 carbon atoms. Examples of long chain fatty acid include oleic acid, palmitic acid, stearic acid and linoleic acid. Preferably, the long chain fatty acid is oleic acid. For example, the present invention provides a compound having the formula

(5)

(6)

(7)

(8)

or combinations thereof, for use to maintain or increase muscle function and/or mass in a subject, and/or prevent or reduce muscle wasting in a subject.

Other examples of triglycerides which may be used in the present invention include: 1,3-dibutyryl-2-linoleoylglycerol, 1,3-dibutyryl-2-stearoylglycerol, 1-butyryl-2-oleoyl-3-palmitoylglycerol, 1-palmitoyl-2-oleoyl-3-butyrylglycerol, 1-butyryl-2-oleoyl-3-linoleoylglycerol, 1-linoleoyl-2-oleoyl-3-butyrylglycerol, 1-oleoyl-2-butyryl-3-linoleoylglycerol, 1-linoleoyl-2-butyryl-3-oleoylglycerol, 1-butyryl-2-linoleoyl-3-oleoylglycerol, 1-oleoyl-2-linoleoyl-3-butyrylglycerol, 1-butyryl-2-stearoyl-3-oleoylglycerol, 1-oleoyl-2-stearoyl-3-butyrylglycerol, 1-butyryl-2-oleoyl-3-stearoylglycerol, 1-stearoyl-2-oleoyl-3-butyrylglycerol, 1,2-dioleoyl-3-palmitoylglycerol, 1-palmitoyl-2,3-dioleoylglycerol, 1,2-dioleoyl-3-linoleoylglycerol and 1-linoleoyl-2,3-dioleoylglycerol.

The triglycerides of the present invention may be synthesised by, for example, esterification of long chain fatty acid(s) and butyric acid with glycerol.

The triglycerides of the present invention may be synthesised by, for example, interesterification between tributyrin and another triglyceride containing long chain fatty acids. In one embodiment, high oleic sunflower oil is the source of the long chain fatty acids. This generates triglycerides containing predominantly butyrate and oleate moieties. The compounds are dairy-free, cholesterol-free and vegan. Fatty acids are liberated from triglycerides due to lipases, naturally present in the gastrointestinal tract. Relative to butyrate salts, the compounds do not add additional mineral salts to the final formulation.

Alternative methods of triglyceride synthesis can be routinely determined by a person skilled in the art. By way of example, a method of obtaining 1,3-dibutyryl-2-palmitoylglycerol (BPB) is shown below:

A single butyrate moiety containing triglyceride may be used herein. Alternatively, a mixture of different butyrate moiety containing triglycerides may be used.

Compositions

Compounds of the present invention may be administered in the form of a composition. Thus, the present invention provides compositions comprising butyrate moiety containing triglycerides referred to herein, for use to maintain or increase muscle function and/or mass in a subject, and/or prevent or reduce muscle wasting in a subject.

In one embodiment, a combination of a compound having formula (1) and a compound having formula (2) is present in the composition as defined herein.

In one embodiment the compound having formula (1) is present in an amount of at least 10% by weight of the total triglycerides in the composition, and the compound having formula (2) is present in an amount of at least 10% by weight of the total triglycerides in the composition.

In one embodiment the compound having formula (1) is present in an amount of at least 15% by weight of the total triglycerides in the composition, and the compound having formula (2) is present in an amount of at least 15% by weight of the total triglycerides in the composition.

In one embodiment the compound having formula (1) is present in an amount of at least 20% by weight of the total triglycerides in the composition, and the compound having formula (2) is present in an amount of at least 20% by weight of the total triglycerides in the composition.

In one embodiment the compound having formula (1) is present in an amount of at least 20% by weight of the total triglycerides in the composition, and the compound having formula (2) is present in an amount of at least 30% by weight of the total triglycerides in the composition.

In one embodiment the compound having formula (1) comprises about 20% to about 40% by weight of the total triglycerides in the composition, and/or the compound having formula (2) comprises about 30% to about 40% by weight of the total triglycerides in the composition.

In one embodiment the compound having formula (1) and the compound having formula (2) comprise at least 20%, 30%, 40%, 50%, 60% or 70% by weight of the total triglycerides in the composition, preferably about 40% to about 80%, or about 50% to about 75% by weight of the total triglycerides in the composition.

In one embodiment the composition further comprises the compound having formula (3), preferably wherein the compound having formula (3) comprises at least 2%, 3%, 4% or 5% by weight of the total triglycerides in the composition, and/or the composition further comprises the compound having formula (4), preferably wherein the compound having formula (4) comprises at least 1%, 2% or 3% by weight of the total triglycerides in the composition.

In one embodiment the compound having formula (1) is present in an amount of at least 20% by weight of the total butyric acid containing triglycerides in the composition, and the compound having formula (2) is present in an amount of at least 30% by weight of the total butyric acid containing triglycerides in the composition.

In one embodiment the compound having formula (1) comprises about 30% to about 50% by weight of the total butyric acid containing triglycerides in the composition, and/or the compound having formula (2) comprises about 40% to about 60% by weight of the total butyric acid containing triglycerides in the composition.

In one embodiment the compound having formula (1) and the compound having formula (2) comprise at least 20%, 30%, 40%, 50%, 60%, 70% or 80% by weight of the total butyric acid containing triglycerides in the composition, preferably about 60% to about 90% by weight of the total butyric acid containing triglycerides in the composition.

In one embodiment the compound having formula (5) comprises at least 10% by weight of the total triglycerides in the composition, and/or the compound having formula (6) comprises at least 10% by weight of the total triglycerides in the composition.

In one embodiment the compound having formula (5) comprises at least 15% by weight of the total triglycerides in the composition, and/or the compound having formula (6) comprises at least 15% by weight of the total triglycerides in the composition.

In one embodiment the compound having formula (5) comprises at least 15% by weight of the total triglycerides in the composition, and/or the compound having formula (6) comprises at least 20% by weight of the total triglycerides in the composition.

In one embodiment the compound having formula (5) comprises at least 20% by weight of the total triglycerides in the composition, and/or the compound having formula (6) comprises at least 20% by weight of the total triglycerides in the composition.

In one embodiment the compound having formula (5) comprises about 15% to about 30% by weight of the total triglycerides in the composition, and/or the compound having formula (6) comprises about 20% to about 30% by weight of the total triglycerides in the composition.

In one embodiment the compound having formula (5) and the compound having formula (6) comprise at least 20%, 30% or 40% by weight of the total triglycerides in the composition, preferably about 30% to about 60%, or about 40% to about 50% by weight of the total triglycerides in the composition.

In one embodiment the composition further comprises the compound having formula (7), preferably wherein the compound having formula (7) comprises at least 2% or 3% by weight of the total triglycerides in the composition, and/or the composition further comprises the compound having formula (8), preferably wherein the compound having formula (8) comprises at least 2% or 3% by weight of the total triglycerides in the composition.

In one embodiment the compound having formula (5) comprises at least 10% by weight of the total butyrate moiety containing triglycerides in the composition, and the compound having formula (6) comprises at least 10% by weight of the total butyrate moiety containing triglycerides in the composition.

In one embodiment the compound having formula (5) comprises at least 15% by weight of the total butyrate moiety containing triglycerides in the composition, and the compound having formula (6) comprises at least 15% by weight of the total butyrate moiety containing triglycerides in the composition.

In one embodiment the compound having formula (5) comprises at least 15% by weight of the total butyrate moiety containing triglycerides in the composition, and the compound having formula (6) comprises at least 20% by weight of the total butyrate moiety containing triglycerides in the composition.

In one embodiment the compound having formula (5) comprises at least 20% by weight of the total butyrate moiety containing triglycerides in the composition, and the compound having formula (6) comprises at least 20% by weight of the total butyrate moiety containing triglycerides in the composition.

In one embodiment the compound having formula (5) comprises about 15% to about 30% by weight of the total butyrate moiety containing triglycerides in the composition, and the compound having formula (6) comprises about 20% to about 30% by weight of the total butyrate moiety containing triglycerides in the composition.

In one embodiment the composition further comprises the compound having formula (7), preferably wherein the compound having formula (7) comprises at least 2% or 3% by weight of the total butyrate moiety containing triglycerides in the composition, and/or the composition further comprises the compound having formula (8), preferably wherein the compound having formula (8) comprises at least 2% or 3% by weight of the total butyrate moiety containing triglycerides in the composition.

In one embodiment composition of the present invention may further comprise 1,3-dibutyryl-2-linoleoylglycerol, 1,3-dibutyryl-2-stearoylglycerol, 1-butyryl-2-oleoyl-3-palmitoylglycerol, 1-palmitoyl-2-oleoyl-3-butyrylglycerol, 1-butyryl-2-oleoyl-3-linoleoylglycerol, 1-linoleoyl-2-oleoyl-3-butyrylglycerol, 1-oleoyl-2-butyryl-3-linoleoylglycerol, 1-linoleoyl-2-butyryl-3-oleoylglycerol, 1-butyryl-2-linoleoyl-3-oleoylglycerol, 1-oleoyl-2-linoleoyl-3-butyrylglycerol, 1-butyryl-2-stearoyl-3-oleoylglycerol, 1-oleoyl-2-stearoyl-3-butyrylglycerol, 1-butyryl-2-oleoyl-3-stearoylglycerol, 1-stearoyl-2-oleoyl-3-butyrylglycerol, 1,2-dioleoyl-3-palmitoylglycerol, 1-palmitoyl-2,3-dioleoylglycerol, 1,2-dioleoyl-3-linoleoylglycerol and/or 1-linoleoyl-2,3-dioleoylglycerol.

In one embodiment tributyrin comprises less than 10% by weight of the total butyrate moiety containing triglycerides in the composition, preferably less than 8% by weight, more preferably less than 5% by weight of the total butyrate moiety containing triglycerides in the composition.

The composition of the present invention can be in, for example, a solid (e.g. powder), liquid or gelatinous form.

The composition of the present invention can be in, for example, tablet, dragee, capsule, gel cap, powder, granule, solution, emulsion, suspension, coated particle, spray-dried particle or pill.

The composition may in the form of a pharmaceutical composition and may comprise one or more suitable pharmaceutically acceptable carriers, diluents and/or excipients. Examples of such suitable excipients for compositions described herein may be found in the "Handbook of Pharmaceutical Excipients", 2nd Edition, (1994), Edited by A Wade and P J Weller. Acceptable carriers or diluents for therapeutic use are also well known in the pharmaceutical art, and are described, for example, in Remington's Pharmaceutical Sciences, Mack Publishing Co. (A. R. Gennaro edit. 1985).

The pharmaceutical compositions may comprise as, or in addition to, the carrier, excipient or diluent any suitable binder(s), lubricant(s), suspending agent(s), coating agent(s) and/or solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like.

Preservatives, stabilisers, dyes and even flavouring agents may be provided in the composition. Examples of preservatives include sodium benzoate, sorbic acid and esters of p-hydroxybenzoic acid. Antioxidants and suspending agents may be also used.

The composition may be a nutritional composition.

The expression "nutritional composition" means a composition that nourishes a subject. This nutritional composition is preferably taken orally, and it may include a lipid or fat source and a protein source. It may also contain a carbohydrate source. In one embodiment, the nutritional composition contains only a lipid or fat source. In other specific embodiments, the nutritional composition contains a lipid (or fat) source with a protein source, a carbohydrate source or both.

In some specific embodiments, the nutritional composition according to the invention is an "enteral nutritional composition" that is to say a foodstuff that involves the gastrointestinal tract for its administration. The gastric introduction may involve the use of a tube through the oro/nasal passage or a tube in the belly leading directly to the stomach. This may be used especially in hospitals or clinics.

In some specific embodiments, the composition is an oral nutritional supplement (ONS), a complete nutritional formula, a pharmaceutical, a medical or a food product. In some specific embodiments, the composition is administered to the individual as a beverage. The composition may be stored in a sachet as a powder and then suspended in a liquid such as water for use.

The composition according to the invention can be a dietary supplement.

The term "dietary supplement" may be used to complement the nutrition of an individual (it is typically used as such but it might also be added to any kind of compositions intended to be ingested). It may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The dietary supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

When the composition is a supplement, it can be provided in the form of unit doses.

The composition according to the invention can be a dairy product, a liquid beverage, a beverage powder, a dehydrated soup, a dietary supplement, a meal replacement, a nutritional bar, a cereal, a confectionery product or a dry pet food.

The composition may further comprise dietary fiber. The "dietary fiber" may comprise at least one non-digestible oligosaccharide (e.g. prebiotics). The prebiotics may be present in an amount between 0.3 and 10% by weight of composition. Dietary fiber and/or prebiotics may promote the production of endogenous butyrate by gut microflora and thus provide additional beneficial effects.

Prebiotics are usually non-digestible in the sense that they are not broken down and absorbed in the stomach or small intestine and thus remain intact when they pass into the colon where they are selectively fermented by the beneficial bacteria. Examples of prebiotics include certain oligosaccharides, such as fructooligosaccharides (FOS), inulin, xylooligosaccharides (XOS), polydextrose or any mixture thereof. In a particular embodiment, the prebiotics may be fructooligosaccharides and/or inulin. In a specific embodiment, the prebiotics is a combination of FOS with inulin such as in the product sold by BEN EO-Orafti under the trademark Orafti® oligofructose (previously Raftilose®) or in the product sold by BENEO-Orafti under the trademark Orafti® inulin (previously Raftiline®). Another example is a combination of 70% short chain fructooligosaccharides and 30% inulin, which is registered by Nestle under the trademark "Prebio 1". The nutritional composition of the invention can also comprise at least one milk's oligosaccharide that can be a BMO (bovine milk oligosaccharide) and/or a HMO (human milk oligosaccharide). In a particular embodiment, the nutritional composition according to the invention comprises an oligosaccharide mixture comprising from 0.1 to 4.0 wt % of N-acetylated oligosaccharide(s), from 92.0 to 98.5 wt % of the galacto-oligosaccharide(s) and from 0.3 to 4.0 wt % of sialylated oligosaccharide(s).

The composition of the present invention can further comprise at least one probiotic (or probiotic strain), such as a probiotic bacterial strain. Consumption of probiotic strains may also promote the production of endogenous butyrate by gut microflora and thus provide additional beneficial effects.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is *Bifidobacteria* and/or *Lactobacilli*.

The nutritional composition according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. It may also be probiotic parts such as cell wall components or products of the probiotic metabolism. There may be both viable probiotics and inactivated probiotics in some other embodiments. The nutritional composition of the invention can further comprise at least one phage (bacteriophage) or a mixture of phages, preferably directed against pathogenic *Streptococci, Haemophilus, Moraxella* and *Staphylococci*.

The nutritional composition of the invention, generally contains a protein source, a carbohydrate source and a lipid source. In some embodiments however, especially if the nutritional composition of the invention is a supplement or a fortifier, there may be only lipids (or a lipid source).

The nutritional composition according to the invention may contain a protein source. Protein sources based on, for example, whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions. In some embodiments the protein source is whey predominant (i.e. more than 50% of proteins are coming from whey proteins, such as 60%> or 70%>). The proteins may be intact or hydrolysed or a mixture of intact and hydrolysed proteins. In some embodiments, the protein source may also be provided partially or entirely in the form of added amino acids.

By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein, which has been hydrolysed or broken down into its component amino acids.

The proteins may be either fully or partially hydrolysed. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10%> by weight of lysine; for example about 7% by weight of lysine which greatly improves the nutritional quality of the protein source.

In one particular embodiment the proteins of the composition are hydrolysed, extensively hydrolysed or partially hydrolysed. The degree of hydrolysis (DH) of the protein can be between 2 and 20, or between 8 and 40, or between 20 and 60 or between 20 and 80 or more than 10, 20, 40, 60, 80 or 90. For example, nutritional compositions containing hydrolysates having an extent of hydrolysis less than about 15% are commercially available from Nestle Company under the trade mark Peptamen®.

In some embodiments the protein is extensively hydrolysed.

At least 70%, 80%, 85%, 90%, 95% or 97% of the proteins may be hydrolysed. In a particular embodiment, 100% of the proteins are hydrolysed.

In one particular embodiment the proteins are provided as amino acids.

In one particular embodiment the proteins of the composition are plant based protein.

The nutritional composition according to the present invention may contain a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used.

The nutritional composition of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B3, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition of the invention may contain emulsifiers and stabilisers such as soy, lecithin, citric acid esters of mono- and diglycerides, and the like. The nutritional composition of the invention may also contain other substances which may have a beneficial effect such as lactoferrin, osteopontin, TGFbeta, sIgA, glutamine, nucleotides, nucleosides, and the like.

The nutritional composition according to the invention may be prepared in any suitable manner. For example, a composition may be prepared by blending together the components in appropriate portions, optionally blended with one or more carriers and then mixing the dry blended mixture with a liquefier to form a liquid mixture. The liquid mixture may then be homogenised, pasteurised and optionally spray-dried if the final product is to be a powder. The composition may be homogenised before pasteurisation or after pasteurisation.

The nutritional composition of the invention can be administered to an individual such as a human, e.g., an elderly human, in a therapeutically effective dose. The therapeutically effective dose can be determined by the person skilled in the art and will depend on a number of factors known to those of skill in the art, such as the severity of the condition and the weight and general state of the individual.

In one embodiment of the invention, the nutrition composition is administered to a subject in combination with a regime of exercise or physical activity.

The nutritional composition of the invention can be formulated to be administered to an animal, in the form of animal treats (e.g., biscuits), or dietary supplements. The compositions may be a dry composition (e.g., kibble), semi-moist composition, wet composition, or any mixture thereof. In another embodiment, the nutritional composition is a dietary supplement such as a gravy, drinking water, beverage, yogurt, powder, granule, paste, suspension, chew, morsel, treat, snack, pellet, pill, capsule, tablet, or any other suitable delivery form.

The nutritional composition may be administered to an individual in an amount sufficient to prevent or at least partially reduce the risk of developing a disease or condition sarcopenia in instances where the condition of sarcopenia has yet not been developed in the individual. Such an amount is defined to be "a prophylactically effective dose." Again, the precise amounts depend on a number of factors relating to the individual, such as their weight, health and how much muscle functionality (e.g. muscle strength, gait speed, etc.) is being lost.

The nutritional composition is preferably administered as a supplement to the diet of an individual daily or at least twice a week. In an embodiment, the composition is administered to the individual consecutively for a number of days, preferably until an increase in muscle functionality (e.g. muscle strength, gait speed, etc.) relative to that before administration is achieved. For example, the composition can be administered to the individual daily for at least 30, 60 or 90 consecutive days. As another example, the composition can be administered to the individual for a longer period, such as a period of 1, 2, 3, 4, 5, 6, 7, 8, 9 or 10 years.

In one preferred embodiment, the nutritional composition is administered to the individual for at least 3 months, for example a period of 3 months to 1 year, and preferably for at least 6 months.

The above examples of administration do not require continuous daily administration with no interruptions. Instead, there may be some short breaks in the administration, such as a break of two to four days during the period of administration. The ideal duration of the administration of the composition can be determined by those of skill in the art.

Cachexia and Related Diseases

The invention provides compounds, compositions and methods of preventing and/or treating cachexia or skeletal muscle wasting syndrome by modulating skeletal muscle stem cells. Cachexia is a complex metabolic syndrome associated with underlying illness and characterized by loss of muscle with or without loss of fat mass. The prominent clinical feature of cachexia is weight loss in adults (corrected for fluid retention) or growth failure in children (excluding endocrine disorders).

Cachexia is often seen in patients with diseases such as cancer, chronic heart failure, renal failure, chronic obstructive pulmonary disease, AIDS, autoimmune disorders, chronic inflammatory disorders, cirrhosis of the liver, anorexia, chronic pancreatitis and/or metabolic acidosis and neurodegenerative disease.

There are certain types of cancer wherein cachexia is particularly prevalent, for example, pancreas, esophagus, stomach, bowel, lung and/or liver cancer.

The internationally recognised diagnostic criterion for cachexia is weight loss greater than 5% over a restricted time, for example 6 months, or weight loss greater than 2% in individuals already showing depletion according to current body weight and height (body-mass index [BMI] <20 kg/m$^2$) or skeletal muscle mass (measured by DXA, MRI, CT or bioimpedance). Cachexia can develop progressively through various stages—precachexia to cachexia to refractory cachexia. Severity can be classified according to degree of depletion of energy stores and body protein (BMI) in combination with degree of ongoing weight loss.

In particular, cancer cachexia has been defined as weight loss >5% over past 6 months (in absence of simple starvation); or BMI <20 and any degree of weight loss >2%; or appendicular lean mass consistent with low muscle mass (males <7.26 kg/m$^2$; females <5.45 kg/m$^2$) and any degree of weight loss >2% (Fearon et al., Lancet Oncology (2011), 12, pp 489-495).

Precachexia may be defined as weight loss 5% together with anorexia and metabolic change. At present there are no robust biomarkers to identify those precachectic patients who are likely to progress further or the rate at which they will do so. Refractory cachexia is defined essentially on the basis of the patient's clinical characteristics and circumstances.

It may be appreciated that the compounds, compositions and methods of the present invention may be beneficial for the prevention and/or treatment of the condition of precachexia as well as cachexia in particular to maintain or improve skeletal muscle mass and/or muscle function.

In one embodiment of the invention, the invention provides a method of treatment of cachexia or precachexia comprising administering to a human or animal subject an effective amount of a compound of the invention.

In another embodiment of the invention, the invention provides a method of treatment of cachexia or precachexia comprising administering to a human or animal subject an effective amount of a compound of the invention wherein cachexia or precachexia is associated with a disease selected from cancer, chronic heart failure, renal failure, chronic obstructive pulmonary disease, AIDS, autoimmune disorders, chronic inflammatory disorders, cirrhosis of the liver, anorexia, chronic pancreatitis, metabolic acidosis and/or neurodegenerative disease.

In a preferred embodiment of the invention, the invention provides a method of treatment of cancer cachexia is associated with cancer is selected from pancreas, esophagus, stomach, bowel, lung and/or liver cancer.

In yet another embodiment of the invention, the invention provides a method of treatment wherein treatment of cancer cachexia is measured by reducing body weight loss, preventing body weight loss, maintaining body weight or increasing body weight.

In another embodiment of the invention, a compound or a composition of the invention may be used in a method of treatment wherein cancer cachexia is a result of treatment for cancer with a chemotherapeutic agent.

In a further embodiment of the invention, a compound or a composition of the invention may be used in a method of prevention or treatment of cachexia in combination with a dietary intervention of high caloric, high protein, high carbohydrate, Vitamin B3, Vitamin B12 and/or Vitamin D supplementation, antioxidants, omega fatty acids, and/or polyphenols.

Sarcopenia and Related Diseases

Sarcopenia can be characterized by one or more of low muscle mass, low muscle strength and low physical performance.

Sarcopenia can be diagnosed in a subject based on the definition of the AWGSOP (Asian Working Group for Sarcopenia in Older People), for example as described in Chen et al., J Am Dir Assoc. (2014), 15(2), pp 95-101. Low muscle mass can generally be based on low appendicular lean mass normalized to height square (ALM index), particularly ALM index less than 7.00 kg/m2 for men and 5.40 kg/m2 for women. Low physical performance can generally be based on gait speed, particularly gait speed of <0.8 m/sec. Low muscle strength can generally be based on low hand grip strength, particularly hand grip strength less than 26 kg in men and less than 18 kg in women.

Sarcopenia can be diagnosed in a subject based on the definition of the EWGSOP (European Working Group for Sarcopenia in Older People), for example as described in Crutz-Jentoft et al., Age Ageing (2010), 39, pp 412-423. Low muscle mass can generally be based on low appendicular lean mass normalized to height square (ALM index), particularly ALM index less than 7.23 kg/m2 for men and 5.67 kg/m2 for women. Low physical performance can generally be based on gait speed, particularly gait speed of <0.8 m/sec. Low muscle strength can generally be based on low hand grip strength, particularly hand grip strength less than 30 kg in men and less than 20 kg in women.

Sarcopenia can be diagnosed in a subject based on the definition of the Foundation for the National Institutes of Health (FNIH), for example as described in Studenski et al., J Gerontol A Biol Sci Med Sci. (2014), 69(5), pp 547-558. Low muscle mass can generally be based on low appendicular lean mass (ALM) normalized to body mass index (BMI; kg/m2), particularly ALM to BMI less than 0.789 for men and 0.512 for women. Low physical performance can generally be based on gait speed, particularly gait speed of <0.8 m/sec. Low muscle strength can generally be based on low hand grip strength, particularly hand grip strength less than 26 kg in men and less than 16 kg in women. Low muscle strength can also generally be based on low hand grip strength to body mass index, particularly hand grip strength to body mass index less than 1.00 in men and less than 0.56 in women.

The D3-creatine dilution method is another approach to measure muscle mass. This method is becoming more widely accepted as a robust standard and potentially a future alternative to DXA. The D3-creatine dilution method has been described previously in Clark et al. J Appl Physiol. (1985), 116(12), pp 1605-1613 and Stimpson et al. J Cachexia Sarcopenia Muscle (2013), 4(3), pp 217-223.

It may be appreciated that the compounds, compositions and methods of the present invention may be beneficial to prevent and/or treat sarcopenia and/or related conditions, in particular, to maintain or improve skeletal muscle mass and/or muscle function.

Myopathy and Related Conditions

Myopathies are neuromuscular disorders in which the primary symptom is muscle weakness due to dysfunction of muscle fiber. Other symptoms of myopathy can include muscle cramps, stiffness, and spasm. Myopathies can be inherited (such as the muscular dystrophies) or acquired (such as common muscle cramps).

Myopathies are grouped as follows: (i) congenital myopathies: characterized by developmental delays in motor skills; skeletal and facial abnormalities are occasionally evident at birth (ii) muscular dystrophies: characterized by progressive weakness in voluntary muscles; sometimes evident at birth (iii) mitochondrial myopathies: caused by genetic abnormalities in mitochondria, cellular structures that control energy; include Kearns-Sayre syndrome, MELAS and MERRF glycogen storage diseases of muscle: caused by mutations in genes controlling enzymes that metabolize glycogen and glucose (blood sugar); include Pompe's, Andersen's and Cori's diseases (iv) myoglobinurias: caused by disorders in the metabolism of a fuel (myoglobin) necessary for muscle work; include McArdle, Tarui, and DiMauro diseases (v) dermatomyositis: an inflammatory myopathy of skin and muscle (vi) myositis ossificans: characterized by bone growing in muscle tissue (vii) familial periodic paralysis: characterized by episodes of weakness in the arms and legs (viii)polymyositis, inclusion body myositis, and related myopathies: inflammatory myopathies of skeletal muscle (ix) neuromyotonia: characterized by alternating episodes of twitching and stiffness; and stiff-man syndrome: characterized by episodes of rigidity and reflex spasms common muscle cramps and stiffness, and (x) tetany: characterized by prolonged spasms of the arms and legs. (Reference: https://www.ninds.nih.gov/disorders/all-disorders/myopathy-information-page).

It may be appreciated that the compounds, compositions and methods of the present invention may be beneficial to prevent and/or treat the aforementioned diseases or conditions, in particular, to maintain or improve skeletal muscle mass and/or muscle function.

Muscular Dystrophy

Muscular dystrophy are a group of genetic diseases characterized by progressive weakness and degeneration of the skeletal or voluntary muscles which control movement. Major types of muscular dystrophy include: Duchenne muscular dystrophy, Becker muscular dystrophy, limb-girdle muscular dystrophy, facioscapulohumeral muscular dystrophy, congenital muscular dystrophy, oculopharyngeal muscular dystrophy, distal muscular dystrophy, Emery-Dreifuss muscular dystrophy and myotonic dystrophy.

(Reference: https://www.medicalnewstoday.com/articles/187618.php)

It may be appreciated that the compounds, compositions and methods of the present invention may be beneficial to prevent and/or treat the aforementioned diseases or conditions, in particular, to maintain or improve skeletal muscle mass and/or muscle function, Recovery after Muscle Injury from Surgery and Muscle Traumas Muscle injuries can be caused by bruising, stretching or laceration causing acute or chronic soft tissue injury that occurs to a muscle, tendon, or both. It may occur as a result of fatigue, overuse, or improper use of a muscle. It may occur after physical trauma such as a fall, fracture or overuse during physical activity. Muscle injuries may also occur after surgery such as joint replacement arthroscopic surgery.

It may be appreciated that the compounds, compositions and methods of the present invention may be beneficial to prevent and/or treat the aforementioned conditions of recovery after surgery and/or muscle trauma, in particular, to maintain or improve skeletal muscle mass and/or muscle function.

Method of Treatment

It is to be appreciated that all references herein to treatment include curative, palliative and prophylactic treatment; although in the context of the invention references to preventing are more commonly associated with prophylactic treatment. Treatment may also include arresting progression in the severity of a disease.

The term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder. As used herein, a subject is "in need of a treatment if such subject would benefit biologically, medically or in quality of life from such treatment.

Subject

The term "subject" means any animal, including humans and companion animals. Generally, the subject is a human or an avian, bovine, canine, equine, feline, hircine, murine, ovine or porcine animal. The subject can be a horse or a companion animal, for example a cat or a dog. Preferably, the subject is a human.

The treatment of mammals, particularly humans, is preferred. However, both human and veterinary treatments are within the scope of the invention.

For veterinary subjects, dogs, cats and equine subjects are preferred.

The present invention may also be useful in non-human animal subjects such as: avian, bovine, ovine or porcine animals, for optimizing meat production by increasing skeletal muscle mass and/or function.

Muscle Stem Cells

The term "muscle stem cell", as used herein, may refer to satellite cells, preferably satellite cells that are quiescent and are uncommitted.

Satellite cells are precursors to skeletal muscle cells. In adult muscle, satellite cells are generally quiescent, but can activate and undergo myogenesis in response to disease or mechanical strain such as injury or exercise. Satellite cells are also involved in the normal growth of muscle. Upon activation, satellite cells proliferate before undergoing myogenic differentiation to finally fuse with existing myofibers or to form new myofibers, depending on the magnitude of tissue trauma. In addition to generating differentiated myogenic progeny, at least some satellite cells can self-renew, thereby meeting the defining criteria of bona fide resident stem cells.

MyoD+ is a commitment marker that may be used to distinguish quiescent from committed satellite cells.

Muscle Function and Mass

The compounds, compositions, uses and methods disclosed herein may provide for the maintenance of or increase in muscle function and/or mass.

The term "muscle function" refers to the ability of a muscle to perform in a manner that does not negatively impact on the life of a subject, and encompasses parameters of muscle strength, muscle contraction, muscle endurance, muscle elasticity, ability of a muscle to resist muscle fatigue and/or physical activities of daily living such as walking up stairs, getting out of a chair and other activities of daily living.

Suitable tests for assessing muscle function include grip strength assessment using a dynamometer; one repeat maximum on leg press, chest press or leg extension; gait speed; 6 min walk test; time up and go; short physical performance battery; Fried frailty criteria; and stair climbing time assessments. Other suitable tests include muscle strength, endurance and time to fatigue.

Muscle mass (which may equate with muscle volume, muscle thickness or myofiber size) may be measured by dual-energy X-ray absorptiometry (DXA) or bioimpedance tests. Similarly, MRI may be used for assessing muscle volume and ultra-sound may be used for assessing muscle thickness and pennation angle.

"Muscle wasting" may be a reduction in muscle mass, for example to the stage where the muscle loss becomes debilitating. In one embodiment, the subject does not lose more than 10%, 5%, 4%, 3%, 2% or 1% of their muscle mass.

Preferably, the compounds, compositions, uses and methods disclosed herein provide for the maintenance of or increase in muscle mass.

The term "maintains" refers to a particular parameter, such as muscle function and/or mass, remaining substantially unchanged over a period of time (e.g. 5, 10, 15, 20, 25, 30, 40, 50 or more years).

In one embodiment, muscle mass increases by at least 1%, 2%, 3%, 4%, 5%, 10%, 15% or 20%.

In another embodiment, muscle mass increases by 1-2.5%, 1-5%, 1-10% or 1-20%.

Preferably, the muscle is skeletal muscle.

Administration

Preferably, the compounds and compositions described herein are administered enterally.

Enteral administration may be oral, gastric, and/or rectal.

In one embodiment the administration is oral or gastric. In a preferred embodiment administration is oral.

In general terms, administration of the combination or composition described herein may, for example, be by an oral route or another route into the gastro-intestinal tract, for example the administration may be by tube feeding.

The subject may be a mammal such as a human, canine, feline, equine, caprine, bovine, ovine, porcine, cervine and primates. Preferably the subject is a human.

Organoleptic Properties

The present invention provides compounds that are a source of butyrate having improved organoleptic properties. In particular, the compounds have improved odor and/or taste relative to butyric acid, butyrate salts and/or tributyrin. In one embodiment, the compounds have improved taste relative to tributyrin. In one embodiment, the compounds have improved smell relative to butyrate salts (e.g. sodium butyrate).

In one embodiment, the improved organoleptic properties are improved odour. In one embodiment, the improved organoleptic properties are improved taste. In one embodiment, the improved organoleptic properties are improved odour and improved taste. In one embodiment, the improved taste is reduced bitterness.

EXAMPLES

Example 1

Preparation of Butyrated Triglycerides (TAG)

Compositions comprising butyrated TAG were generated by chemical interesterification between tributyrin and high oleic sunflower oil in the presence of catalyst such as sodium methoxyde. A molar excess of tributyrin compared to high oleic sunflower oil was be used.

The three reagents, tributyrin, high oleic sunflower oil and the catalyst were mixed together into a reactor under nitrogen atmosphere and then heat under stirring at 80° C. for 3 h. Once the reaction is completed, the product was washed several times with water then dried under vacuum (25 mBar at 60° C. for 2 h). The resulting oil product was then subjected to a decoloration step with the action of bleaching earth and was purified either by short-path distillation (130° C., 0.001-0.003 mbar) or by deodorisation (160° C., 2 mbar, 2 h) with injection of steam water.

The constituents, mostly triglycerides, of the resulting oil compositions are shown below in Table 1. These triglycerides are represented by the three fatty acids they contain. These fatty acids are represented by their lipid number: 4:0 for butyrate, 16:0 for palmitate, 18:0 for stearate, 18:1 for oleate and 18:2 for linoleate. The fatty acid in the middle is located on the position sn-2 in the triglyceride. As an example, 16:0-4:0-18:1 stands for two different triglycerides having both a butyrate in position sn-2 and either a palmitate in position sn-1 and an oleate in position sn-3 or an oleate in position sn-1 and a palmitate in position sn-3.

TAG profile and regioisomers were analyzed by liquid chromatography coupled to high resolution mass spectrometer. Lipid classes' proportion was evaluated by liquid chromatography coupled to evaporative light scattering detector (ELSD).

TABLE 1

| TAG regioisomer profile [g/100 g] | |
|---|---|
| TAG regioisomer [g/100 g] | |
| | Composition |
| 4:0-4:0-4:0 | <0.4-4.7 |
| 4:0-16:0-4:0 | 0.8-1.0 |
| 4:0-18:2-4:0 | 4.0-6.3 |
| 4:0-4:0-18:1 | 3.0-6.1 |
| 4:0-18:1-4:0 | 16.2-27.0 |
| 4:0-18:0-4:0 | 0.8-1.3 |
| 4:0-22:0-4:0 | ≤0.4 |
| 4:0-16:0-18:1 | 1.1-1.5 |
| 16:0-4:0-18:1 | 0.5-0.7 |
| 4:0-18:1-16:0 | 1.2-1.6 |
| 4:0-18:1-18:2 | 2.6-3.1 |
| 18:1-4:0-18:2 | 1.1-1.6 |
| 4:0-18:2-18:1 | 2.9-3.6 |
| 18:1-18:1-4:0 | 23.3-25.8 |
| 18:1-4:0-18:1 | 3.3-4.8 |
| 4:0-18:0-18:1 | 0.9-1.3 |
| 4:0-18:1-18:0 | 0.8-1.1 |
| 4:0-22:0-18:1 | <0.4-0.5 |
| 18:1-18:1-16:0 | 0.6-1.4 |
| 18:1-18:1-18:2 | 1.3-1.5 |
| 18:1-18:2-18:1 | 0.5-0.7 |
| 18:1-18:1-18:1 | 6.1-10.7 |
| 18:1-18:1-18:0 | 0.5-0.8 |
| Total | 93.1-94.1 |

In the Composition samples, the two most abundant TAG are 4:0-18:1-4:0 and 18:1-18:1-4:0, they represent together approximately 40 to 50 g/100 g.

Example 2

Odor Properties of Butyrate Moiety Containing Triglycerides

An odor comparison of a solution including butyrate moiety containing TAG (composed mainly with oleic and butyric fatty acids) was compared to a solution containing sodium butyrate.

Sample Preparation

Solutions including butyrate moiety containing TAG (see Example 1) or sodium butyrate were prepared and stored at 4° C. prior to delivery to the sensory panel. Each 250 mL solution contained 600 mg of butyric acid (equivalent to one capsule of commercially available sodium butyrate as a supplement; 2.4 mg/mL concentration) and 1% w/v BEBA Optipro 1 infant formula in acidified, deionized water.

The samples were prepared the day before the test, by putting 4 mL of each solution (TAG butyrate solution; sodium butyrate solution) in Agilent vials.

Methodology

The 'two-out-of-five test' was performed. In this test, the panellist is given five samples. The panellist is instructed to identify the two samples that are different from the other three. The presentation order of the samples is randomized in order to avoid presentation order bias.

In addition to the two-out-of-five test, a comment box was presented to the panellists to allow them to comment about the nature of the difference perceived (e.g. odour intensity, odour quality).

Results

The five samples were presented simultaneously to the panellists. They were asked to uncap, smell and then cap each vial in a given order. The results are shown in Table 2.

TABLE 2

| Number of responses | Number of correct responses | Significance |
|---|---|---|
| 11 | 9 | p < 0.0001*** |

P-value was calculated using a binomial test performed with Fizz software (Biosystemes, France).

The panellists who found the correct responses (butyrate moiety containing TAG different from sodium butyrate) mentioned that the sodium butyrate smells "cheese" whereas for the butyrate moiety containing TAG samples this "cheese" smell was considerably decreased and the odour was quite neutral.

Example 3

Taste Properties of Butyrate Moiety Containing Triglycerides

Sensory benchmarking of a solution including butyrate moiety containing TAG (see Example 1) composed mainly with oleic and butyric fatty acids was performed versus a solution containing tributyrin.

Sample Preparation:

One scoop (4.6 g) of BEBA Optipro 1 infant formula was added to warm water (cooled, boiled tap water as per instructions) to a final volume of 150 mL (approximately 3% w/v solution). Each TAG form of butyrate was weighed separately to deliver 600 mg of butyrate, and the addition of infant formula to a final volume of 50 mL for each solution was performed.

Solution A included butyrate moiety containing TAG (see Example 1); and solution B contained tributyrin.

Methodology

A group of panellists performed a repeated blind-coded tasting.

The samples were prepared just prior to the preliminary bitterness assessment, and each solution was vigorously shaken. Tasting cups labelled A and B were filled at the same time with a small volume of the respective solution.

The two samples were presented simultaneously to the panellists. They were asked to taste the solution in a sip and spit fashion, and rank the perceived bitterness on a scale from 0-10; where 0 is no bitterness perceived and 10 resembles the maximum imaginable bitterness.

Results

Bitterness of Solution A was ranked by panellists at 4.33±1.52, mean±SD.

Bitterness of Solution B was ranked by panellists at 8.33±1.52, mean±SD.

These data show that the butyrate moiety containing TAG composition in infant formula was notably less bitter in taste as compared to tributyrin in infant formula.

Example 4

Taste properties 1,3-dibutyryl-2-palmitoylglycerol 1,3-dibutyryl-2-palmitoylglycerol (BPB) was synthesized as a single compound using the following synthesis:

BPB was evaluated in a descriptive sensory panel evaluation and found to be neutral in taste and odor.

Example 5

Digestion of Butyrate Moiety Containing Triglycerides 5.1 Emulsion Preparation 10 wt % oil in water emulsions stabilised by 0.3 wt % polyoxyethylene sorbitan mono-oleate (Tween® 80) were prepared by mixing the Tween 80 into the oil phase at 40° C., then mixing with the water phase. An emulsion was then created using an ultrasonic probe homogeniser.

5.2 Granulometry

The droplet size of each lipid emulsion was measured by laser light scattering using a Mastersizer 3000 equipped with a Hydro SM from Malvern Instruments (Malvern, Worcestershire, United Kingdom). Emulsion particle sizes are quoted as two values, the volume surface mean diameter $D_{3,2}$ ($D_{3,2}$ ¼ Pnidi 3/nidi 2) or the volume length mean diameter $D_{4,3}$ ($D_{4,3}$ ¾ Pnidi 4/nidi 3). Emulsion particle size results are an average of three measurements of two freshly prepared emulsions.

5.3 In Vitro Digestion

The lipid emulsion (2 mL) containing 200 mg of fat was subjected to gastrointestinal in vitro lipolysis. The digestions were conducted in thermostated glass vessels (37° C.) in a pH-STAT setup controlled by a TIM 856 bi-burette pH-STAT (Radiometer Analytical, France). For gastric digestion, the sample was incubated for 90 minutes with 8.5 mL of simulated gastric fluid (SGF), which consisted of 150 mM NaCl, 450 U/mL pepsin, 18 U/mL rabbit gastric lipase at 37° C. and a pH of 5.5. The digestion was initiated by adding 18 tributyrin U/ml (TBU) activity determined at pH 5.4) of rabbit gastric lipase.

The intestinal digestion step was performed in the pH stat where the pH was kept constant at 6.8 by addition of NaOH. A bile salt mixture (bile salts prepared with tris buffer) and calcium solution (20 mM Ca, 176 5 mM tris, 150 mM NaCl) were added to the SGF-sample mixture. This mixture was transferred to the pH-stat, where the pH was adjusted to approximately 6.78. The intestinal digestion step starts when the temperature reaches 37±0.5° C. The pH was adjusted to pH 6.8 and after incubation of two minutes at this pH and temperature, a pancreatin solution was added. The final composition of the intestinal fluid was 10 mM CaCl$_2$, 12 mM mixed bile salts, 0.75 mM phospholipid, 150 mM NaCl and 4 mM tris(hydroxymethyl)aminomethane buffer. The intestinal digestion step was carried out for 3 hours in a titration manager from Radiometer. During the intestinal phase of digestion, the kinetics of digestion were followed using a pH-stat (TIM856, Radiometer) technique and expressed as titratable acid (rather than fatty acid) that was calculated by the equation:

$$TA = V_{NaOH} \times 0.05 \times 1000$$

TA: Total titratable acid released, mmol; $V_{NaOH}$: volume of NaOH used to titrate the released acid in 3 h, mL.

5.6 Results

Since the digestion of dietary lipids involves lipases of both gastric and intestinal origin, lipid digestibility was assessed using two digestion models i) simulated intestinal fluid (SIF) with porcine pancreatic lipase (PPL) and ii) sequential digestion in simulated gastric fluid (SGF) with rabbit gastric lipase (RGL) followed by simulated intestinal fluid (SIF) with porcine pancreatic lipase (PPL). All lipids were emulsified using polyoxyethylene sorbitan mono-oleate (Tween® 80) and had similar particle size distributions and specific surface areas (FIG. 2), meaning the differences in digestion are predominately arising from the triglyceride molecular structure.

Figure 1:
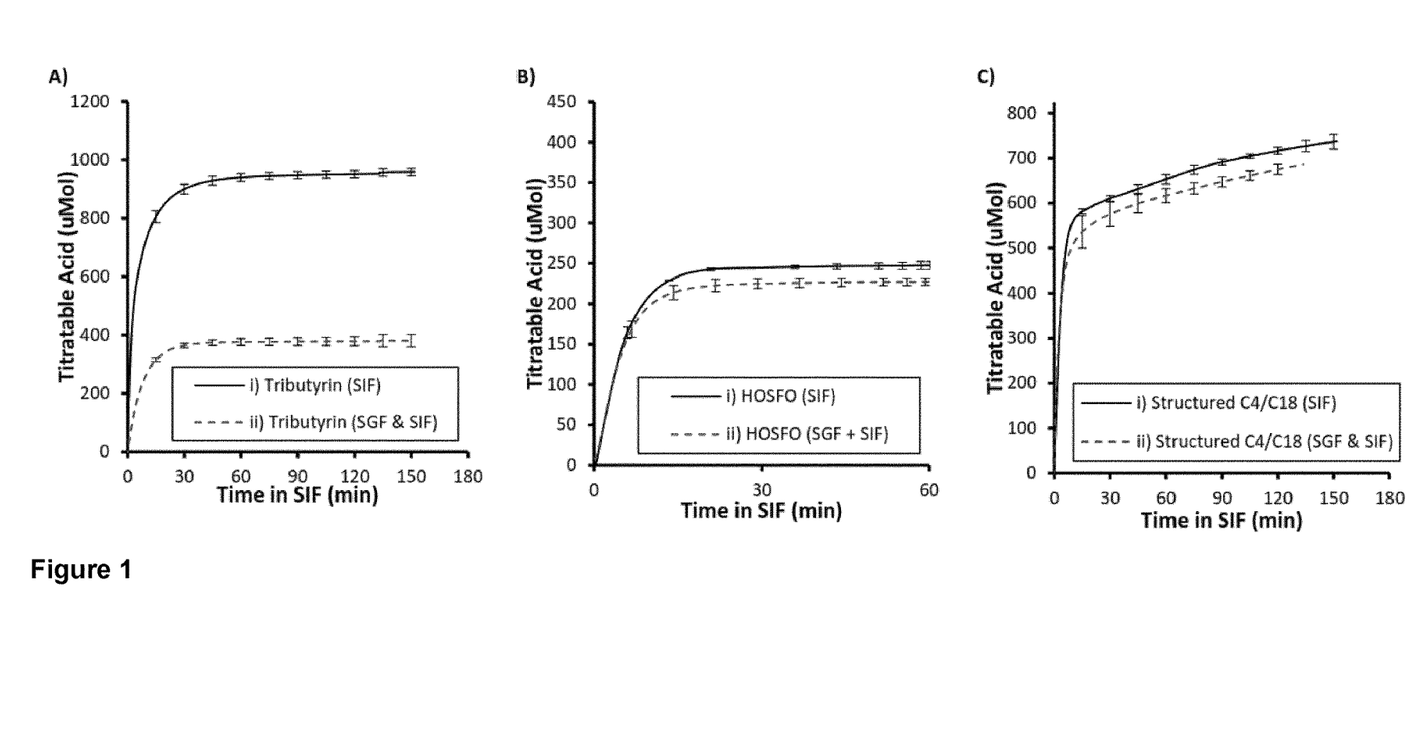
FIG. 1 shows the release of fatty acid from emulsions containing 200 mg of (A) tributyrin, (B) high oleic sunflower oil and (C) a mixture of butyrate moiety containing triacylglycerol (TAG) according to the invention, digested either with i) simulated intestinal fluid (SIF) or (ii) sequentially with gastric fluid (SGF) followed by simulated intestinal fluid (SIF).

FIG. 1$i$ A-C shows the digestion of tributyrin (C4), high oleic sunflower oil (HOSFO, largely C18:1) and butyrate moiety containing triglycerides according to the invention, generated by chemical interesterification between tributyrin and high oleic sunflower oil (see Example 1) "C4-C18:1", by porcine pancreatic lipase (from pancreatin) in the presence of mixed bile and calcium (SIF model). The lipids generally exhibit the same lipolysis behaviour, undergoing an initial rapid period of lipolysis during the first 15 minutes which progressively slows during the final 2.5 hours of simulated intestinal digestion. C4 triglyceride exhibited an initial maximal rates of lipolysis of 223±59 µmol·min$^{-1}$. The initial rate of lipolysis for the high oleic sunflower oil, 34.5±2.3 µmol·min$^{-1}$ was significantly lower (p<0.0001) than the short chain triglyceride. C4-C18:1 exhibited an initial rate of hydrolysis of 153±47 µmol·min$^{-1}$, between that of the C4 and C18:1. Overall, it is seen that all of the triglycerides are rapidly and extensively digested in the presence of porcine pancreatic lipase.

The triglycerides were next digested using the sequential SGF (RGL) SIF (PPL) model, the digestion in the SIF compartment is shown in FIG. 1$ii$ A-C. No measurements were taken in the gastric compartment due to limited ionisation of the target fatty acids. Compared to when they were digested with SIF alone, the C4 and C18:1 triglycerides generally released a lower amount of titratable acid during 3 hours of digestion. The effect is largest with tributyrin, which has a significantly lower (p<0.0001) initial lipolysis rate 44.1±8.8 µmol·min$^{-1}$ during SGF-SIF digestion compared to SIF alone 223±59 µmol·min$^{-1}$. The total amount of acid released after SGF-SIF digestion of tributyrin 381±20 µmol, is almost ⅓ the amount released after SIF only digestion, 958±12.5 µmol. These results clearly indicate that there is considerable digestion of tributyrin within the gastric compartment of the model.

When sequentially exposed to SGF and SIF, the SIF lipolysis rates of the butyrate moiety containing triglycerides C4-C18:1 is 124±20 µmol·min$^{-1}$, showing a slight but not significant decrease compared to SIF alone (124±20 µmol·min$^{-1}$). The most interesting observation is the influence of secondary fatty acid chain length on the decrease in SIF lipolysis caused by RGL pre-exposure. Originally, tributyrin exhibited a 60.2% (147±7.6 µmol) decrease in total fatty acid release during SIF lipolysis after pre-exposure to RGL in SGF. In comparison, the C4-C18:1 interesterified triglycerides exhibited a 6.1% (45±7.6 µmol) decrease.

Figure 2:
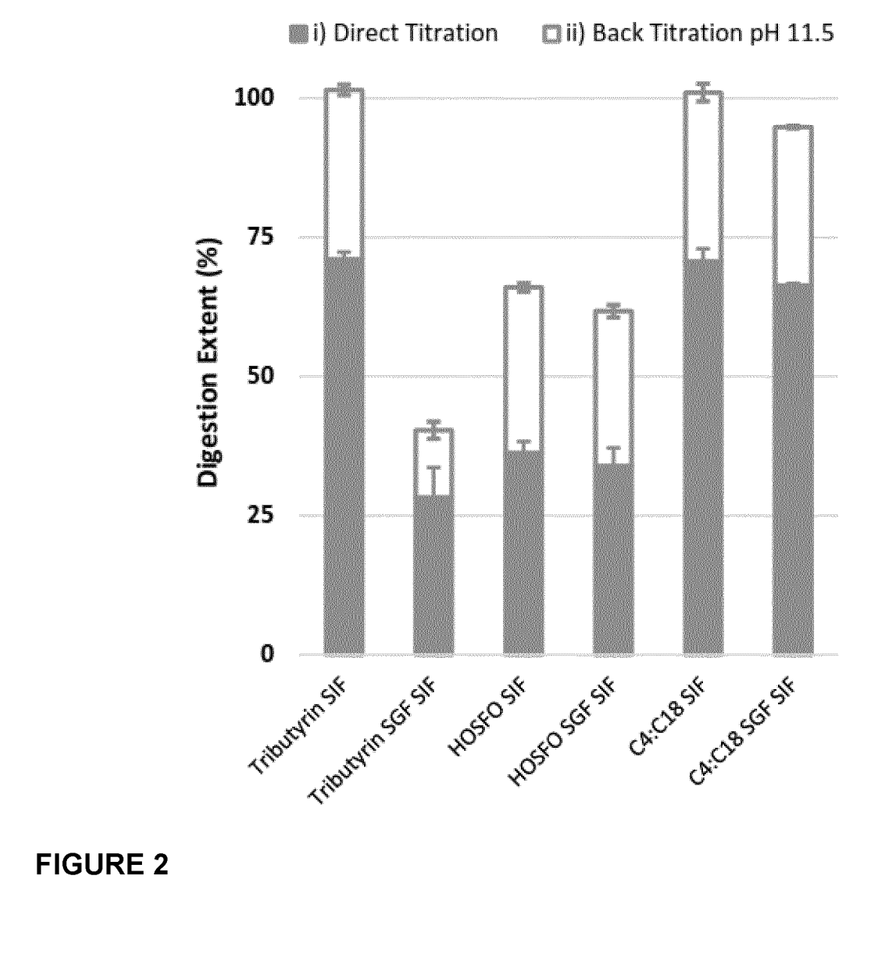
FIG. 2 shows the overall extent of lipid digestion after both SIF and SGF-SIF for tributyrin, high oleic sunflower oil and a mixture of butyrate moiety containing TAG according to the invention.

The overall extent of lipid digestion after both SIF and SGF-SIF is presented in FIG. 2 for the three triglycerides using direct and back titration. Because many fatty acids are only partially ionised at pH 6.8, direct titration gives only partial picture of the extent of lipid digestion, instead back titration to pH 11.5 or GC-FAME analysis is required to estimate the full extent of digestion. Results of the back titration for the three triglycerides show that tributyrin and the butyrate moiety containing triglycerides C4-C18:1 underwent 101.5±0.9% and 101±1.6% digestion respectively, indicating release of three fatty acids per molecule for complete digestion, whilst high oleic sunflower oil underwent 72.3±2% digestion indicating release of two fatty acids per molecule for complete digestion.

Overall, it was seen that tributyrin underwent extensive hydrolysis in the stomach, whilst high oleic sunflower oil triglyceride underwent very limited hydrolysis in the stomach. Surprisingly, it was seen that butyrate moiety containing triglycerides generated via interesterification of C4 with long chain fatty acids (C4-C18:1) decreases the extent of gastric lipolysis of C4 fatty acids. Tributyrin underwent ~60% lipolysis by gastric lipase as indicated by decreased total fatty acid release during SIF lipolysis after pre-exposure to RGL in SGF. In comparison, the C4-C18:1 butyrate moiety containing triglycerides exhibited only a 6.1% decrease in total fatty acid release in SGF-SIF. These results suggest that interesterification of C4 with long chain fatty acids (C4-C18:1) modulates the release of butyric acid within the stomach to later in the intestine following digestion, and that the design of structured lipids alter the timing (but not extent) of short chain fatty acid delivery in the gastrointestinal tract.

Example 6

Muscle Stem Cell Commitment

Figure 3A:
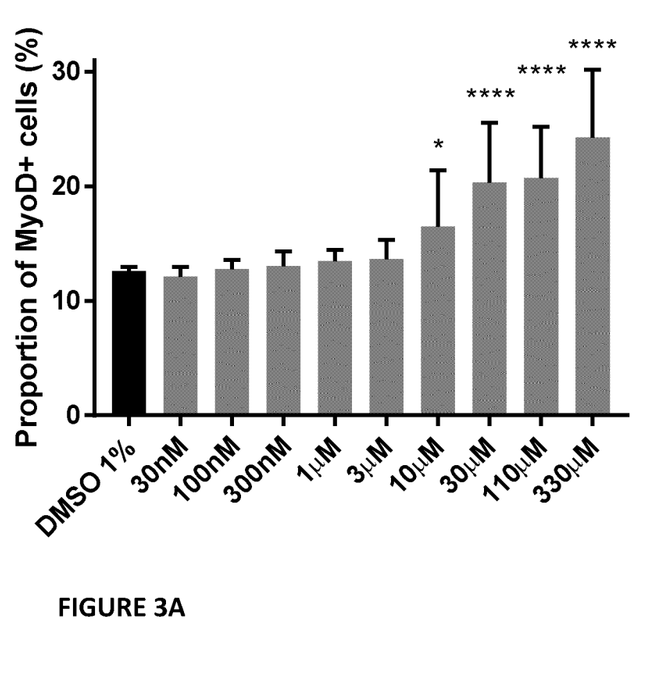
FIGS. 3A and 3B represents the proportion of MyoD+ cells for donors 8 and 4 respectively.
Figure 3B:
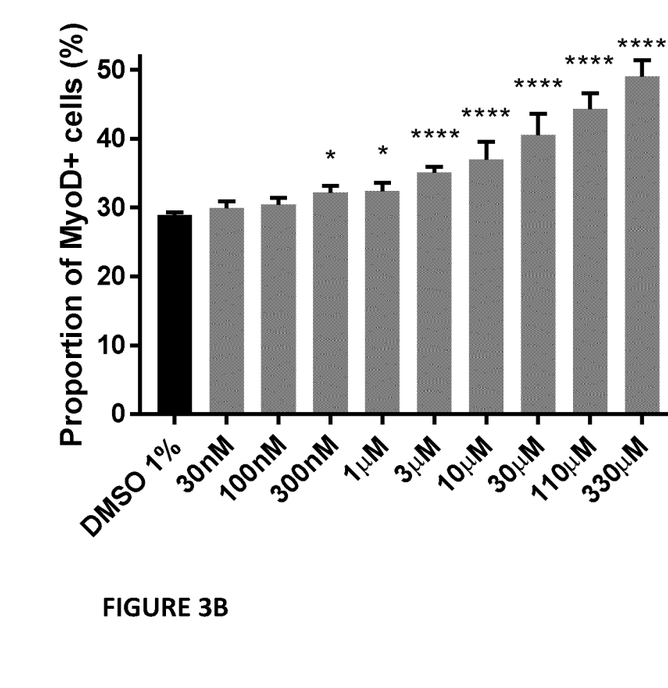

Human primary myoblasts from two different donors (donor 8 & donor 4) were seeded in 384 well plates at a density of 1'000 cells per well in skeletal muscle growth medium (SKM-M, AMSbio). For treatment, compounds were directly added to the myoblast cultures 16 hours after initial plating. All cultures were then grown for 96 hours. Cells were stained for Pax7 and MyoD expression using antibodies directed against Pax7 and MyoD and counterstained with Hoechst 33342 to visualize cell nuclei. Myoblasts (MyoD+) are defined as cells that do not express Pax7 but express MyoD. Image acquisition was performed using the ImageXpress (Molecular Devices) platform. Custom module analysis based on Multi-Wavelength Cell Scoring of the MetaXpress software was used for quantification. For each condition, the total number of cells was determined to evaluate compound toxicity, and the number of MyoD+ cells was normalized to the total cell number in order to evaluate the proportion of this population. *, , *, **** indicates difference from the control (DMSO 1%), One-way ANOVA, with p<0.05, p<0.01, p<0.001, p<0.0001, respectively. Data are presented as Mean +/− SEM FIG. 3 shows the results for butyrate (sodium burtyrate), with MyoD+ cells normalized to the total cell number in order to evaluate the myogenic commitment. Whereby, it is seen that butyrate promotes muscle stem cell differention.

All publications mentioned in the above specification are herein incorporated by reference. Various modifications and variations of the disclosed methods, cells, compositions and uses of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

The invention claimed is:

1. A method for maintaining or increasing skeletal muscle function and/or mass and preventing or reducing muscle wasting, the method comprising administering to an individual in need of same a compound having the formula (1)

[structure]

(2)

[structure]

(3)

[structure], or (4)

[structure], or combinations thereof, wherein $R^1$, $R^2$, $R^3$, $R^4$, $R^5$ and $R^6$ are independently an acyl group of a long chain fatty acid having between 16 and 20 carbons.

2. A method for maintaining or increasing skeletal muscle function and/or mass and preventing or reducing muscle wasting comprising administering to an individual in need of same a composition comprising a compound having the formula (1)

[structure]

(2)

[structure]

(3)

[structure], or (4)

[structure], or combinations thereof, wherein $R^1$, $R^2$, $R^3$, $R^4$, $R^5$ and $R^6$ are independently an acyl group of a long chain fatty acid having between 16 and 20 carbons.

3. The method according to claim 2, wherein the composition comprises the compound having formula (1), the compound having formula (2), the compound having formula (3) and the compound having formula (4).

4. The method according to claim 2, wherein the compounds having formula (1), (2), (3) and (4), comprise at least 50% by weight of the total triglycerides of the composition.

5. The method according to claim 2, wherein the compounds having formula (1), (2), (3) and (4), comprise at least 50% by weight of the total butyrate moiety containing triglycerides in the composition.

6. The method according to claim 2, wherein tributyrin comprises less than 10% by weight of the total triglycerides in the composition.

7. The method according to claim 2, wherein the composition further comprises vitamin D and/or protein.

8. The method according to claim 2, wherein the composition is a nutritional composition, a dietary supplement or a pet care product.

9. The method according to claim 1, wherein $R^1$, $R^2$, $R^3$, $R^4$, $R^5$ and/or $R^6$ is an unsaturated fatty acid.

10. The method according to claim 2, wherein $R^1$, $R^2$, $R^3$, $R^4$, $R^5$ and/or $R^6$ is selected from the group consisting of oleic acid, palmitic acid, and linoleic acid.

11. The method according to claim 1, wherein the method modulates muscle stem cell function.

12. The method according to claim 2, wherein the method substantially prevents or reduces muscle wasting in the individual.

13. The method according to claim 1, for (i) treatment or prevention of cachexia, precachexia, sarcopenia, myopathy, and/or dystrophy, and/or (ii) recovery after muscle injury or surgery.

14. The method according to claim 13, wherein the cachexia is associated with a disease selected from the group consisting of cancer, chronic heart failure, renal failure, chronic obstructive pulmonary disease, AIDS, autoimmune disorders, chronic inflammatory disorders, cirrhosis of the liver, anorexia, chronic pancreatitis, metabolic acidosis and neurodegenerative disease.

15. The method according to claim 13, wherein cachexia or precachexia is associated with cancer.

16. A method of treatment for cachexia or precachexia, the method comprising administering to a human or animal subject an effective amount of a compound having the formula or combinations thereof, wherein $R^1$, $R^2$, $R^3$, $R^4$, $R^5$ and $R^6$ are independently an acyl group of a long chain fatty acid having between 16 and 20 carbons.

17. The method according to claim 16, wherein treatment of cachexia is measured by reducing body weight loss, preventing body weight loss, maintaining body weight or increasing body weight.

18. The method according to claim 9, wherein $R^1$, $R^2$, $R^3$, $R^4$, $R^5$ and/or $R^6$ is monounsaturated.

19. The method according to claim 2, wherein the method modulates muscle stem cell function.

20. The method according to claim 1, wherein the method substantially prevents or reduces muscle wasting in the individual.

21. The method according to claim 2, for (i) treatment or prevention of cachexia, precachexia, sarcopenia, myopathy, dystrophy, and/or (ii) recovery after muscle injury or surgery.

* * * * *